United States Patent [19]

Fujiwara et al.

[11] Patent Number: 5,422,920
[45] Date of Patent: Jun. 6, 1995

[54] CRYSTAL GRAIN SIZE ESTIMATING METHOD FOR NUCLEAR FUEL PELLETS

[75] Inventors: Noboru Fujiwara; Masaki Mori; Chikatsu Isaka, all of Ibaraki, Japan

[73] Assignee: Mitsubishi Nuclear Fuel Company, Ltd., Tokyo, Japan

[21] Appl. No.: 211,908
[22] PCT Filed: Aug. 30, 1993
[86] PCT No.: PCT/JP93/01217
 § 371 Date: Apr. 26, 1994
 § 102(e) Date: Apr. 26, 1994
[87] PCT Pub. No.: WO94/06124
 PCT Pub. Date: Mar. 17, 1994

[30] Foreign Application Priority Data

Sep. 8, 1992 [JP] Japan .................................. 4-265328

[51] Int. Cl.$^6$ ............................................. G21C 17/06
[52] U.S. Cl. ................................... 376/245; 376/261
[58] Field of Search ............... 376/245, 247, 248, 258, 376/260, 261; 264/0.5; 423/261

[56] References Cited

U.S. PATENT DOCUMENTS 4,873,031 10/1989 Yato et al. .................... 264/0.5

FOREIGN PATENT DOCUMENTS 54-19520 7/1979 Japan .

*Primary Examiner*—Daniel D. Wasil
*Attorney, Agent, or Firm*—McAulay Fisher Nissen Goldberg & Kiel

[57] ABSTRACT

A method of estimating the crystal grain size of a nuclear fuel pellet. A plurality types of $UO_2$ powders are heated at a predetermined temperature raising speed in dry air so as to measure weight change ratios occurring due to the oxidation of each of the $UO_2$ powders. From a value at which the weight change ratio changes, a temperature at which the composition of the powder from the $UO_{2+x}$ phase to the $U_3O_7$ phase is determined for each type of the powders. Sintered pellets are produced from the plurality types of $UO_2$ powders in which the arrival temperatures are known. Crystal grain sizes of the plurality types of the sintered pellets produced are measured. According to the $U_3O_7$ phase arrival temperature determined and the crystal grain size of the sintered pellet measured, a correlation between the both is recognized. A $U_3O_7$ phase arrival temperature of a $UO_2$ powder of a test sample is determined under the same conditions as described above. According to the phase arrival temperature and the above-mentioned correlation, a crystal grain size of the $UO_2$ powder of the test sample upon production into a sintered pellet is estimated.

The crystal grain size of a $UO_2$ sintered pellet manufactured from the $UO_2$ powder can be estimated from the oxidation behavior of the $UO_2$ powder without actually manufacturing the sintered pellet. Thereby the measurement cost for the crystal grain size can be reduced.

3 Claims, 2 Drawing Sheets

CRYSTAL GRAIN SIZE ESTIMATING METHOD FOR NUCLEAR FUEL PELLETS

TECHNICAL FIELD

The present invention relates to a method for estimating crystal grain sizes of uranium dioxide ($UO_2$) sintered pellets to be used as nuclear fuel. In particular, it relates to a method for estimating crystal grain sizes of $UO_2$ sintered pellets according to oxidation behavior of $UO_2$ powder.

BACKGROUND ART

Such $UO_2$ sintered pellets are tightly enclosed in coating tubes made of zircaloy, and are used as nuclear fuel.

Recently, in order to make the life of the nuclear fuel to be long to enable continuous operation for a long period of light water reactors or fast breeder reactors, it is advanced to realize a high degree of combustion of nuclear fuel. When the nuclear fuel is allowed to have a high degree of combustion, the amount of fission products (FP) generated from nuclear fuel pellets is increased. Among the products, gaseous one such as radon (Rn) scarcely make solid solutions in the matrix of the nuclear fuel pellet, which diffuse into the crystal grain boundary and generate bubbles there. Swelling occurs due to the bubble formation, and the volume of the pellet increases to give stress to the coating tube. This makes a cause to generate a mechanical interaction (PCI, Pellet Clad Interaction) between the pellet and the coating tube. In addition, the FP gas diffused into the grain boundary is released to the exterior of the pellet later, which increases the internal pressure of the fuel rod to make a cause to decrease the thermal conductivity of the gap between the pellet and the coating tube.

In order to prevent the increase in PCI and the decrease in the thermal conductivity, it has been attempted that the nuclear fuel pellet is allowed to have a large grain size so as to enclose the FP gas in the pellet. This is based on the fact that although the generation of the FP gas itself cannot be suppressed, when the pellet is allowed to have a large grain size, for example, when the crystal grain size is made to be two-fold, the arriving distance to the grain boundary of the FP gas generated in the crystal grain becomes two-fold, and consequently the release speed of the FP gas becomes half.

Until now, methods for increasing the crystal grain size of the $UO_2$ sintered pellet have been disclosed in Unexamined Published Japanese Patent Application No. 2-242195/1990; Unexamined Published Japanese Patent Application No. 3-287096/1991; Unexamined Published Japanese Patent Application No. 4-70594/1992 and the like.

According to these methods, nuclear fuel pellets having crystals of a large grain size of 20–120 $\mu m$ are obtained.

In the prior art, not only for the nuclear fuel pellets produced by these methods as a matter of course, but also for nuclear fuel pellets produced by other methods, the crystal grain size has been mainly measured by a cross-sectional method defined in accordance with ASTM E-112.

In this cross-sectional method, at first a produced $UO_2$ sintered pellet is embedded in a synthetic resin, the pellet embedded in the resin is cut, and then its cross section is polished. Next, a wet etching treatment is performed to expose crystal grain boundaries of the pellet, and then the crystal grain boundaries are photographed by an optical microscope or the like. Next, in a state in which a scale line having a predetermined length is projected on a screen using a slide type projector, a photographed negative film is projected on the same screen so as to overlay a grain boundary texture to the scale line. The number of grains intersecting the scale line on the screen is measured at a plurality of places by sliding the negative film, and an average value of crystal grain sizes is determined according to the grain number.

However, in the above-mentioned cross-sectional method, there is such an advantage that the crystal grain size of the $UO_2$ sintered pellet is directly observed by the photographing with the optical microscope or the like, and a value relatively having a high accuracy is obtained, but on the contrary, it is necessary that every time when the measurement is performed, the $UO_2$ powder is placed in a mold frame to conduct formation and calcination to make the sintered pellet, as well as complicated works for preparation of the measurement are required, and fine operation and observation must be performed.

For example, when $UO_2$ sintered pellets having large crystal grain sizes are produced for a high degree of combustion of nuclear fuel, in order to decrease the ratio of deficiency of the sintered pellets, it is necessary to perform judgment of the suitability of raw material powders for the sintered pellets beforehand. However, in the case of the conventional measurement method, there has been such a problem that relatively much time is consumed for this judgment, and consequently management cost for the raw material powder is raised.

An object of the present invention is to provide a method for estimating crystal grain sizes of $UO_2$ sintered pellets without actually producing $UO_2$ sintered pellets.

Another object of the present invention is to provide a method for estimating crystal grain sizes of nuclear fuel pellets in which when $UO_2$ sintered pellets having large crystal grain sizes are produced for realizing a high degree of combustion of nuclear fuel, the judgment of suitability of raw material powders for the sintered pellets can be performed rapidly and economically.

DISCLOSURE OF THE INVENTION

In order to achieve the above-mentioned objects, a method for estimating crystal grain sizes of nuclear fuel pellets according to the present invention includes the following procedures as shown in FIG. 1.

(a) heating a plurality types of $UO_2$ powders of a predetermined amount at a predetermined temperature raising speed in dry air of a constant flow amount, thereby measuring weight change ratios occurring due to the oxidation of each of the $UO_2$ powders;

(b) determining for each kind of $UO_2$ powders a temperature at which a composition of the powder arrives at from the $UO_{2+x}$ phase to the $U_3O_7$ phase, on the basis of a change in the weight change ratios;

(c) producing $UO_2$ sintered pellets from the plurality types of $UO_2$ powders in which the arrival temperatures are known;

(d) measuring the crystal grain sizes of the plurality types of the sintered pellets produced in (c);

(e) recognizing a correlation between the $U_3O_7$ phase arrival temperature determined in (b) and the crystal grain size of the sintered pellet measured in (d);

(f) determining a $U_3O_7$ phase arrival temperature of a $UO_2$ powder of a test sample under the same conditions as those in (a) and (b); and (g) estimating a crystal grain size of the $UO_2$ powder of the test sample upon production into a sintered pellet, according to the $U_3O_7$ phase arrival temperature determined in (f) and the correlation determined in (e).

The above-mentioned procedures of (a) to (e) of the present invention are basic procedures for determining the correlation between the $U_3O_7$ phase arrival temperature of the $UO_2$ powder and the crystal grain size of the sintered pellet produced with the powder, and the above-mentioned procedures of (f) and (g) are procedures for estimating the crystal grain size of the sintered pellet produced from the $UO_2$ powder of the test sample. Once when the above-mentioned basic procedures of (a) to (e) are established only the above-mentioned procedures (f) and (g) for estimating the crystal grain size of the sintered pellet of the $UO_2$ powder of the test sample are performed repeatedly.

At first, a predetermined amount of the $UO_2$ powder is heated at a predetermined temperature raising speed while allowing a constant amount of dry air to flow, thereby it is oxidized by oxygen in the dry air. As the $UO_2$ powder to be oxidized, in order to provide different values of $U_3O_7$ phase arrival temperature described hereinafter as far as possible, a plurality types of powders having various average grain sizes are prepared. It is known that when the $UO_2$ powder is oxidized under the above-mentioned condition, the powder changes from the $UO_{2+x}$ phase to the $U_3O_7$ phase, which ultimately becomes the $U_3O_8$ phase to be stabilized. The phase-change of the powder can be known from the change ratio of the powder weight, so that the weight change ratio of the powder is measured. This measurement is performed by means of a commonly used thermogravimetric analysis apparatus (thermobalance). The weight change ratio is determined by measuring an increment in weight per unit time because the temperature raising speed is constant.

According to the value at which the weight change ratio changes, the temperature of the arrival from the $UO_{2+x}$ phase to the $U_3O_7$ phase is determined. It is preferable that the arrival temperature is determined, after drawing an oxidation curve of the $UO_2$ powder as shown in FIG. 2, from a inflection point P of the curve. In FIG. 2, the axis of ordinate is the weight change ratio, and the axis of abscissa is the oxidation temperature. The inflection point Q indicates the $U_3O_8$ phase arrival temperature.

Using raw materials of a plurality types of $UO_2$ powders having different $U_3O_7$ phase arrival temperatures, sintered pellets are produced respectively under the same condition by means of a known method. Concretely, the production is performed such that a lubricant is added to the $UO_2$ powder to perform powder-pressing formation to provide a green pellet, next the lubricant is removed, and thereafter sintering is performed in a hydrogen gas flow at a specified temperature in a range of 1400°–1800° C.

The crystal grain sizes of produced plurality types of $UO_2$ sintered pellets are measured by means of the following method. At first the produced $UO_2$ sintered pellet is embedded in a synthetic resin, the pellet embedded in the resin is cut, and thereafter its cross section is polished. Next, after the polishing, an etching treatment is performed to expose crystal grain boundaries, and the measurement is performed by the above-mentioned cross-sectional method using a negative film photographed by an optical microscope or the like. As the synthetic resin in which the $UO_2$ sintered pellet is embedded, acrylic type, silicone type, vinyl type and the like can be exemplified, however, the acrylic type is preferable.

The $U_3O_7$ phase arrival temperatures of the $UO_2$ powder before the production of the sintered pellets and the values of the crystal grain sizes determined by the above-mentioned cross-sectional method are plotted on a chart shown in FIG. 3, and a curve R, which indicates a correlation between the $U_3O_7$ arrival temperature and the crystal grain size of the sintered pellet, is drawn.

On the basis of the obtained correlation, a $UO_2$ powder for which the crystal grain size is intended to be estimated is prepared. The $UO_2$ powder as a test sample is heated under the same condition as that of (a) as described above so as to measure its weight change ratio, and using the same procedure as (b) as described above its $U_3O_7$ phase arrival temperature is determined from its oxidation curve. The determined $U_3O_7$ phase arrival temperature is attributed to the curve R showing the above-mentioned correlation, and the crystal grain size upon production into a sintered pellet of the $UO_2$ powder of the test sample is estimated.

Incidentally, in the present invention, the weight change ratio is used as a parameter for obtaining the oxidation curve of the $UO_2$ powder, however, according to an oxidation curve using a parameter of a calorific value corresponding to chemical energy required during change of crystals of uranium oxide, it is also possible to determine the temperature of arrival from the $UO_2$ powder to the $U_3O_7$ phase.

BEST MODE FOR CARRYING OUT THE INVENTION

An example of the present invention will be explained in detail on the basis of the drawings.

Figure 1:
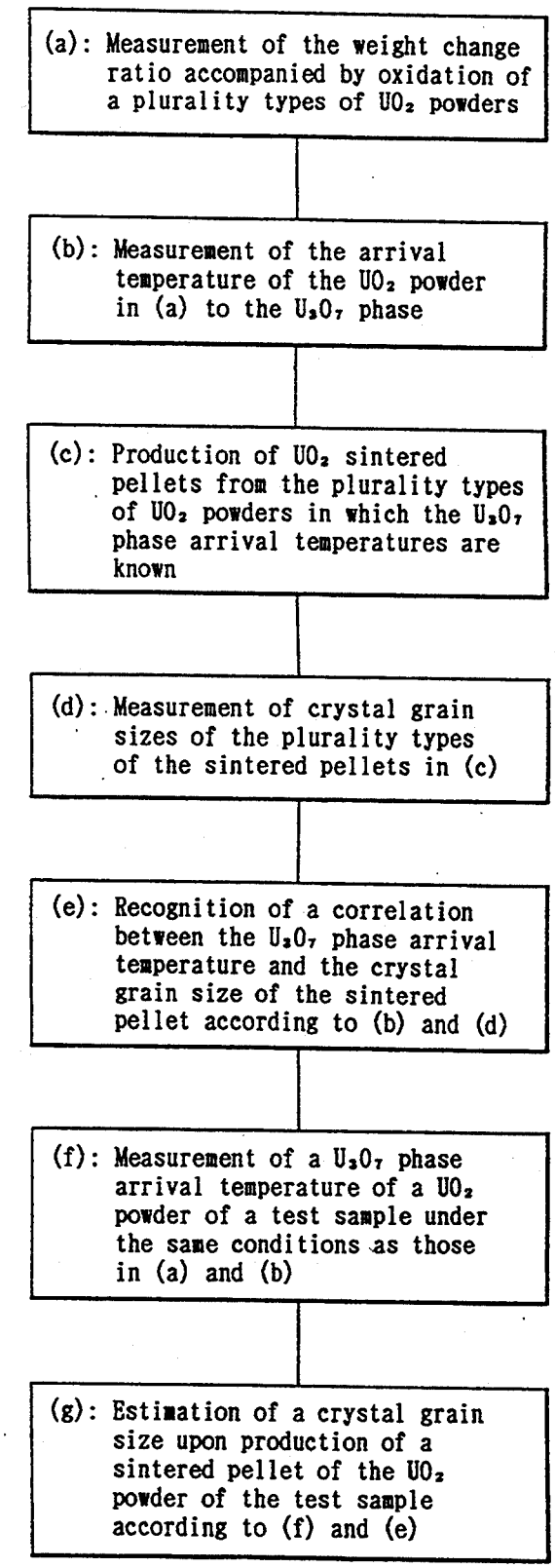
FIG. 1 is a block diagram showing procedures to estimate the crystal grain size of nuclear fuel pellets according to the present invention.
Figure 2:
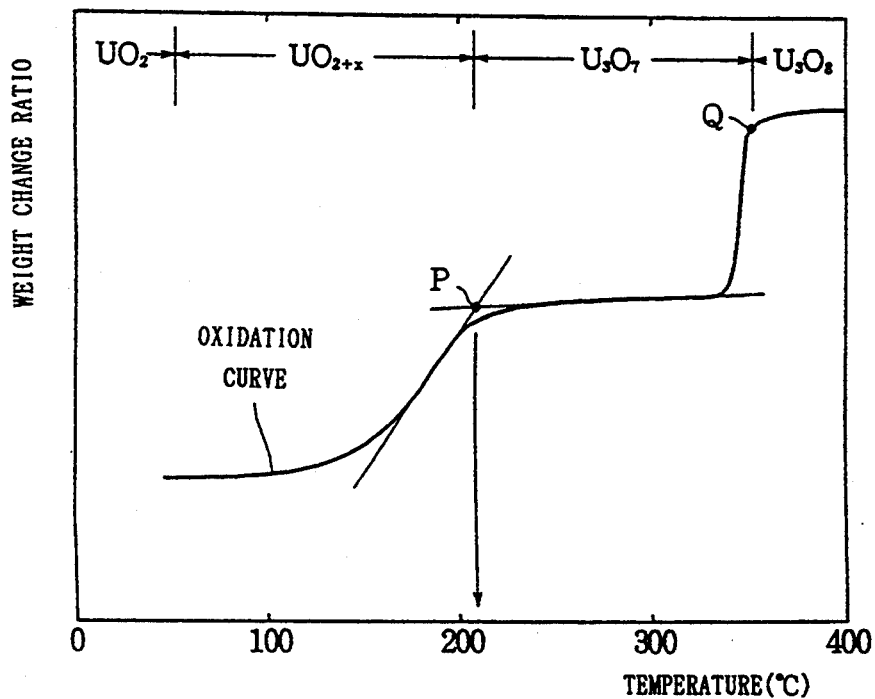
FIG. 2 is an illustrative view of one example of the $UO_2$ powder oxidation curve.

16 types of $UO_2$ powders having different average particle sizes were weighed by about 10 mg respectively using a chemical balance. The weighed $UO_2$ powder was individually placed into a quartz boat of a thermogravimetric analysis apparatus (TBA-50 model, made by Shimadzu Corporation), and after inputting the weighed value into this apparatus, heating was performed under the following heating condition, and the weight change ratio with respect to the heating temperature was determined. The heating and measurement were performed systematically under automatic control, and 16 types of oxidation curves were obtained. One example thereof is shown in FIG. 2.

Air flow amount at the inlet of the apparatus: 10 mL/minute

Moisture of dry air (dew point): not more than $-70°$ C.

Temperature of initiation of temperature raising: room temperature

Temperature raising speed: $2°$ C./minute

According to inflection points P initially appearing in the oxidation curves, temperatures of the arrival of the powders to the $U_3O_7$ phase were determined respectively. In this example, the arrival temperatures of the 16 types of the $UO_2$ powders to the $U_3O_7$ phase were distributed in a wide range from about $170°$ C. to about $250°$ C.

From the above-mentioned 16 types of the $UO_2$ powders were produced 16 individuals of $UO_2$ sintered pellets by means of the following method. At first, 0.2% of zinc stearate was added to and mixed with the $UO_2$ powder as a lubricant, and this mixture was placed in a mold to form a green pellet having a diameter of 10 mm and a height of 15 mm under a pressure of about 2 t/cm$^2$. Next, this formed article was sintered in a hydrogen gas flow at $1750°$ C. for 5 hours to obtain a $UO_2$ sintered pellet.

Next, the obtained $UO_2$ sintered pellet was placed in a cylindrical container, an acrylic ester resin was poured around it to embed the pellet in the resin, and thereafter bubbles in the resin were removed using a reduced-pressure pump. Subsequently the pellet embedded in the resin was cut. Its cut face was polished. and then the polished face is etched with a hydrofluoric acid solution to expose crystal grain boundaries. The exposed crystal grain boundaries were observed with an optical microscope, and a negative film of the crystal grain boundaries was manufactured.

Figure 3:
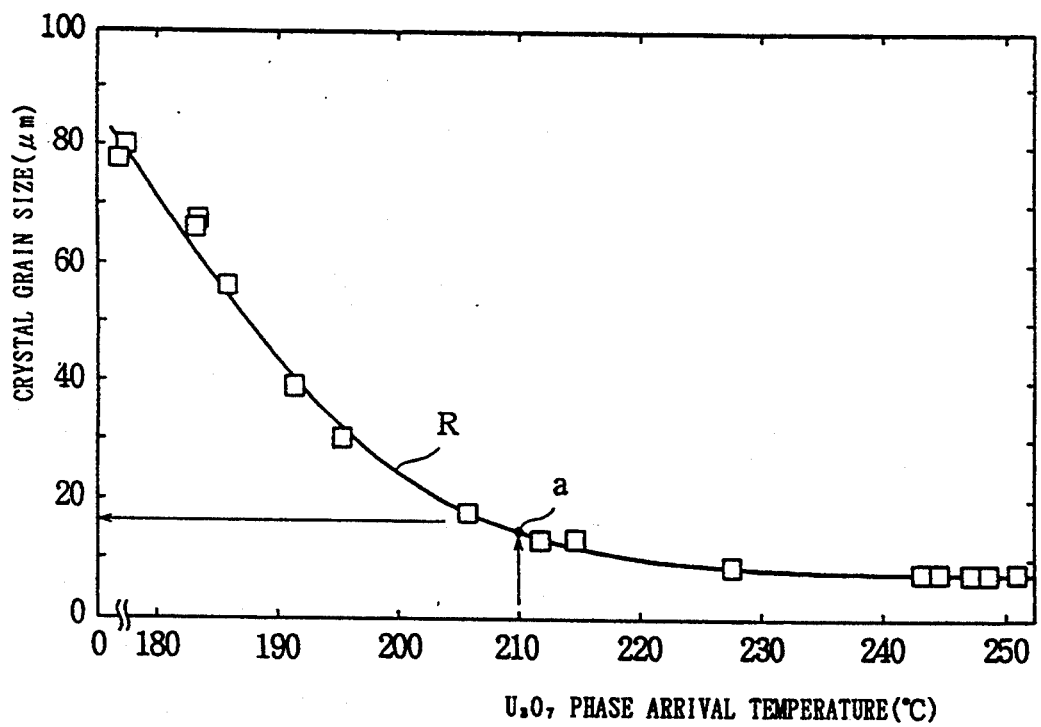
FIG. 3 is an illustrative view of the correlation between the $U_3O_7$ phase arrival temperature and the crystal grain size of the $UO_2$ sintered pellet.

Using this negative film, according to the cross-sectional method in accordance with ASTM E-112, crystal grain sizes were measured from 16 individuals of the $UO_2$ sintered pellets respectively. A relation between the arrival temperatures to the $U_3O_7$ phase of the above-mentioned 16 types of the $UO_2$ powders and the crystal grain sizes of the $UO_2$ sintered pellets manufactured from each of the $UO_2$ powders was plotted, and a curve R showing the correlation between the $U_3O_7$ phase arrival temperature and the crystal grain size shown in FIG. 3 was obtained.

Subsequently, about 10 mg of a $UO_2$ powder of a test sample was weighed, and the thermogravimetric analysis was performed by means of the same operation as described above to obtain an oxidation curve. As shown in FIG. 2, the temperature of arrival of this powder to the $U_3O_7$ phase was $210°$ C. according to an inflection point P initially appeared on the oxidation curve. This temperature of $210°$ C. was allowed to correspond to the axis of abscissa in FIG. 3, and according to an intersection (a) with the curve R, it was estimated that a $UO_2$ sintered pellet to be manufactured from the $UO_2$ powder of the test sample was estimated to have a crystal grain size of about 18 μm.

In order to confirm reliability of the present invention, when a $UO_2$ sintered pellet was manufactured in the same manner as described above using the same $UO_2$ powder as the above-mentioned test sample, and the crystal grain size was directly measured by means of the above-mentioned cross-sectional method, then the crystal grain size was about 19 μm. Thereby it was found that the crystal grain size of the $UO_2$ sintered pellet estimated by the present invention is approximately coincident with the crystal grain size measured directly, and the present invention is a reasonable estimating method.

As described above, according to the present invention, when the crystal grain size of the $UO_2$ sintered pellet manufactured from the $UO_2$ powder is determined, the crystal grain size can be estimated from the oxidation behavior of the $UO_2$ powder without actually manufacturing a sintered pellet. Thereby the measurement cost for the crystal grain size can be reduced.

Especially, when a $UO_2$ sintered pellet having a large crystal grain size is produced in order to realize a high degree of combustion of nuclear fuel, the judgment of suitability of a raw material powder for the sintered pellet can be performed rapidly and economically, and the ratio of occurrence of an unexpected sintered pellet having a small crystal grain size can be suppressed to be low.

INDUSTRIAL APPLICABILITY

The method of the present invention is useful for rapidly and economically performing the judgment of suitability of raw material powders for sintered pellets having large crystal grain sizes for realizing a high degree of combustion of nuclear fuel.

We claim:

1. A method for estimating crystal grain sizes of nuclear fuel pellets comprising:
   (a) heating a plurality types of $UO_2$ powders of a predetermined amount at a predetermined temperature raising speed in dry air of a constant flow amount, thereby measuring weight change ratios occurring due to the oxidation of each of the $UO_2$ powders;
   (b) determining for each kind of $UO_2$ powders a temperature at which a composition of the powder arrives at from the $UO_{2+x}$ phase to the $U_3O_7$ phase, on the basis of a change in the weight change ratios;
   (c) producing $UO_2$ sintered pellets from the plurality types of $UO_2$ powders in which the arrival temperatures are known;
   (d) measuring the crystal grain sizes of the plurality types of the sintered pellets produced in the (c);
   (e) recognizing a correlation between the $U_3O_7$ phase arrival temperature determined in the (b) and the crystal grain size of the sintered pellet measured in the (d);
   (f) determining a $U_3O_7$ phase arrival temperature of a $UO_2$ powder of a test sample under the same conditions as those in the (a) and (b); and
   (g) estimating a crystal grain size of the $UO_2$ powder of the test sample upon production into a sintered pellet, according to the $U_3O_7$ phase arrival temperature determined in the (f) and the correlation determined in the (e).

2. The method for estimating crystal grain sizes of nuclear fuel pellets according to claim 1 wherein the value at which the weight change ratio changes in said (b) is determined, after drawing an oxidation curve of the $UO_2$ powder, from an inflection point of the curve.

3. The method for estimating crystal grain sizes of nuclear fuel pellets according to claim 1 wherein the measurement of the crystal grain size of the sintered pellet in said (d) is performed such that a cross section of the $UO_2$ sintered pellet is polished, thereafter an etching treatment is performed to expose crystal grain boundaries, and image information obtained by an optical microscope or a scanning type electron microscope is used by means of a cross-sectional method.

* * * * *